United States Patent [19]

Slabas et al.

[11] Patent Number: 6,150,586
[45] Date of Patent: Nov. 21, 2000

[54] PLANT GENE ENCODING ACETYL COENZYME A CARBOXYLASE BIOTIN CARBOXYL CARRIER PROTEIN

[75] Inventors: Antoni Ryszard Slabas, Durham; Kieran Michael Elborough, Cleveland, both of United Kingdom

[73] Assignee: Zeneca Limited, London, United Kingdom

[21] Appl. No.: 08/983,409

[22] PCT Filed: Aug. 6, 1996

[86] PCT No.: PCT/GB96/01894

§ 371 Date: Jan. 20, 1998

§ 102(e) Date: Jan. 20, 1998

[87] PCT Pub. No.: WO97/07222

PCT Pub. Date: Feb. 27, 1997

[30] Foreign Application Priority Data

Aug. 18, 1995 [GB] United Kingdom ............... 9516961

[51] Int. Cl.$^7$ .............. A01H 5/00; C12N 15/82; C07H 21/04
[52] U.S. Cl. .......... 800/281; 800/286; 800/298; 435/419; 435/468; 536/23.6
[58] Field of Search ................. 800/281, 286, 800/298; 435/69.1, 419, 468, 320.1; 536/23.6

[56] References Cited

U.S. PATENT DOCUMENTS 5,767,362  6/1998  Best ........................... 800/306

*Primary Examiner*—Elizabeth F. McElwain
*Attorney, Agent, or Firm*—Liza D. Hohenschutz

[57] ABSTRACT

The capacity of a plant to produce fatty acids is modulated by controlling the expression of a gene specifying the acetyl CoA carboxylase biotin carboxyl carrier protein. Modulation may comprise increasing the expression of the gene by insertion of additional copies into the genome or inhibiting expression by insertion of an antisense or cosuppression vector directed against the endogenous gene.

9 Claims, No Drawings

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 842 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO:1:

```
TCTGAAGGAA AGGATGAAAA CTCATCGAAA GACCCTTCTT CTTCGACTGA TTTAGCTACA      60

GAAGAGTCTA TCTCTGAGTT CCTTACCCAA GTAACAACTC TCGTCAAGCT TGTGGATTCG     120

AGAGACATTG TGGAGTTGCA GTTGAAACAA CTCGACTGTG AACTTGTCAT TCGAAAAAAG     180

GAAGCTTTGC CACAACCCGA GTCCCCTGCG CAATATGTTA TGATGCAGCA ACCAAACCAA     240

TCATCTTATG TGCAATCAGT GGCTCCTCCT TCTGCACCTG CTGCATCACC AGCACCTTCT     300

ACTCCTGCCT CTTCACCTAC ACATCTCCAC TACTCCAGCT ACTCATCGCT TCCTACTGTT     360

AAAAGCCCCA TGGCTGGCAC ATTCTACCGT AGTCCAGGAC CTGGCGAACC ACCCTTTATT     420

AAGGTTGGAG ACAAAGTGCA GAAGGGACAA GTTCTATGCA TCGTTGAAGC TATGAAGTTA     480

ATGAATGAAA TAGAGTCTGA CAACGGAACC GTAGTGGATA TCGTTGCAGA GATGCAACCT     540

GTTAGCCTCG ACACTCCTCT GTTTGTGGTT CAACCGTAGA ATCGGCACCA TGAGAAGTGG     600

AGAAAAGAGG CTACTTGTGT CCTGAGACTA CTTCTTGAGA CTCTTGTGTC CTTTTCGTTG     660

TTACCGTTAA AAGTCTGTTA GTTTTTTCTT TTGGTTCGAT GAGGGAGGTG GTTAAAGAAG     720

ATGAGAGCTC TGTTTTATTG ACACACGAAT CTTTGGTTCT GTTTTTTTGC AATTTTCTAT     780

ATCAAATTTT TTTATCACCC TCTCCCAACC ACACGCTCTC GTCTCCCTCG CAGAGTTTCA     840

TA                                                                     842
```

(2) INFORMATION FOR SEQ ID NO:2:

(i) SEQUENCE CHARACTERISTICS:

(A) LENGTH: 421 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

GGGCTGCAGG AATTCGCGGC CGCTGGTGAA CCACCCTTTA TCAAGGTTGG AGACAAAGTG       60

CAGAAGGGAC AAGTTCTATG CATCGTTGAA GCCATGAAGC TAATGAATGA AATAGAGTCT      120

GATCAAACGG GAACCGTAGT GGATATCGTT GCAGAAGATG GCAAGCCTGT TAGTCTCGAC      180

ACTCCTCTGT TTGTGGTTCA ACCGTAGAAT CGACACCACG AGAGATGGAG TAAAGAGGGC      240

TACTTTAAAT CGATCTATGT GCTTTGGTAA TACTGTTTCT TGAGTTTAAG AATGTGTCTT      300

CTTCATTTGT TACTGTCAAA CTCTGTTAGT TTTTTTTTTT GGTCTGGTGA GGAAGAAAGA      360

GTTTTTAGTT TCTATTGGTT AAACAAAAAA AAAGATGAG GCTATGTTTT ATTTTTTTC        420

A                                                                      421

(2) INFORMATION FOR SEQ ID NO:3:

(i) SEQUENCE CHARACTERISTICS:
        (A) LENGTH: 924 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:3:

CCCCCCTCGA GGTCGACGGT ATCGATAAGC TTGATATCGA ATTCGCGGCC GCTGGAATTG       60

CTTGAGGAGT CTGAAAGGAG TTAACTTTGA TTCTCGTACT CGAATCTAAG CAAATGGCGT      120

CTTCGTTCTG GAACATAGCT TATCAACAAG CCATGAGAAG CGGTGTGTTT GTGGCGAAAG      180

TCTACTCCTT TCTCCATATA ACCACTAACT ATCTCGCCTT CCCTGCTTAT GCTTTTGGTC      240

CGAGCTCGAT GATGCCTCCT CCTCCAATGG CAGGCCTTCC AATGCCTCCA TCTCCACCAG      300

TGTCTCTTCC TGCTCCCTCC TCAGCTCCTG CAACAGAAAA ACCAGCAACT GCGCCATCAT      360

CTTCTCATCC ACCACTGAAG AGTCCTATGG CTGGTACTTT CTACAGATCT CCTGGACCCG      420

GTGAACCCCC TTTTGTCAAG GTTGGAGATA AGGTGCAGAA GGGTCAAGTT GTTTGCATTA      480

TTGAAGCTAT GAAACTGATG AACGAGATTG AGGCTGAGAA GTCAGGAACC ATCACCGAGT      540

TACTGGCTGA AGATGGAAAA CCGGTCAGCG TTGATACGCC TCTGTTTACC ATCGTTCCTT      600

GAAATGAAGA AGCTGTCATT TTAGCTGGTT CAGAACACCT ACTTCAAACT CTTGGTTTAG      660

CTATACCAAC GTGCTGACAA TCGTTAAAAA GTAATTATTT CTGTCAGGCT GGTTTGGTTA      720

TGGTTGTCTT TTTTTTTTAT TAAAAAAAAC TTTCTGAACT GTCACCTTCT GTTGAGAATC      780

ACGTAACATA TCAGATTTAC AAGGTGAAAG GCTTGGAGG AGGCTGAACG ATTGGAAGTT       840

TCGACATGGT TACATTTCCA GTAATCACAT TCTGAGCGGC CGCGAATTCC TGCAGCCCGG      900

GGGATCCACT AGTTCTAGAG CGGC                                             924

(2) INFORMATION FOR SEQ ID NO:4:

(i) SEQUENCE CHARACTERISTICS:
        (A) LENGTH: 1001 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:4:

| | | | | | |
|---|---|---|---|---|---|
| ATTTCATCTG | TCTCAACAAT | GGCGTCATTG | TCTGTACCTT | ACGCCAAGAT | CTCTGCCCCA | 60 |
| AACCGTCGGG | TTGGATCTAT | TCCTGGAAGA | ACCCGATGGC | AGCCGCAACT | CAATGGCGTC | 120 |
| TCCTTTCCTT | CCGATGTATC | TCAGAATCAA | TCTACAATCT | GGAGGTTGCG | TGCGACAACC | 180 |
| AACGAGGTTG | TCTCTAACTC | TACCCCAGTG | ACTAACGGTG | GGTGCTTGAA | CGGGAACGTG | 240 |
| AAGAGCAATG | TTCCTGAATC | CGCTAAACTC | TCTAACTTTA | TGGCTAAAGT | TTCAGGTCTT | 300 |
| CTTAAGCTTG | TGGATTCAAG | AGATATAGTG | GAACTTGAAC | TTAAGCAGCT | CGACTGTGAG | 360 |
| ATTGTTATTC | GAAAGAAGGA | AGCTTTACAG | CAGCAACCTA | CACCACCACC | AGCTCCAGTT | 420 |
| TATCACTCCA | TGGCTTCTCC | AATGGCAGGG | CTTCAAATGG | CTCCATCTCA | ACCAGTTGCT | 480 |
| CCTCCTCCTT | TTTCTCTAGT | CCTCTCAGCC | CCTGAAACAG | CAAAACCAGT | AACCCCACCT | 540 |
| TCCTCTTTCA | CATCCTCCAC | TCAAGAGTCC | TATGGGCTGG | GTACTTTCTA | CAGATCTCCT | 600 |
| GGTCCTGGTG | AACCTCCTTT | TGTCAAGGTT | GGAGATAAGG | TGCAGAAGGG | TCAAGTTGTT | 660 |
| TGCATTATTG | AAGCTATGAA | ACTCATGAAT | GAGATTGAGG | CTGAGAAATC | AGGAACCATC | 720 |
| ACTGAACTAC | TAGCTGAAGA | TGGAAAACCG | GTTAGCGTTG | ACACGCCTCT | GTTTACCATC | 780 |
| GTGCCTTGAA | GCGTCATTTT | AGCTGGTCAG | ACATCTTCAA | GTCTTGGTTT | AGCTAATACC | 840 |
| GACGTGCTGA | AATCATAAAG | TAATGTTTCG | GTCATATGGT | TTGGTTTGTT | CGTTTTTTTG | 900 |
| TTTTTCCTCA | CCTTTTGTAT | GAATCACGTG | ACGTATTAAT | ATTGCATGTT | TTAAGATAAT | 960 |
| TTCGACCAAA | CAATTCAGTT | TACAAAAAAA | AAAAAAAAA | A | | 1001 |

(2) INFORMATION FOR SEQ ID NO:5:

(i) SEQUENCE CHARACTERISTICS:
        (A) LENGTH: 1133 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | | | | | |
|---|---|---|---|---|---|
| CAATAGTGTA | AAACATCTCT | CTCTACCATC | TCTTCTTCGT | CGTGCTTCCT | CGGTTACATC | 60 |
| GTCAAAGTGC | ATTTTCATCC | TATCTCAACA | ATGGCGTCAT | TGTCGGTTCC | TTACGCCAAG | 120 |
| ATCTCTGCTC | CTAACCGGCG | GGTCGAATCT | ATTCCTGGGA | TCCGACGGCA | GCCTCAACCC | 180 |
| AGTGGGATCT | CTTTTCACGT | CTCCCATGTA | TCTCAGACTC | AATCTACAAT | CTGGAGGTTG | 240 |
| CGTGCCACAA | CCAATGAGGT | TGTGTCTAAT | TCTACACCAG | TGACTAACGG | TGGATGTTTG | 300 |
| AACGGAAACG | TCAAGACCAA | TGTTCCTCCT | GAACCCGCCG | CCGAGCTCTC | TGACTTTATC | 360 |
| TCTAAAGTCT | CTGGTCTTCT | TAAGCTTGTG | GATTCAAGAG | ATATAGTGGA | ACTTGAGTTG | 420 |
| AAGCAGCTCG | ACTGTGAGAT | TGTTATTCGG | AAGAGGAAGC | TTACCGCAGC | AACAGCTCCA | 480 |
| GTTTATCACT | CGATGATGCC | TCCTCCTCCA | ATGGAAGGCC | TTCCAATGCC | TCCATCTCCA | 540 |
| CCAGTGTCTC | CTCCTGCTCC | CTCCTCAGCT | CCTGCAACAG | CGAATACAGC | AACCGCACCA | 600 |
| TCCTCTTCTC | ATCCTCCACT | GAAGAGTCCT | ATGGCTGGTA | CTTTCTACAG | GTCTCCTGGA | 660 |
| CCCGGTGAAC | CTCCTTTTGT | CAAGGTCGGA | GATAAAGTGC | AGAAGGGTCA | AGTTGTTTGC | 720 |
| ATTATCGAAG | CTATGAAACT | GATGAATGAG | ATTGAGGCTG | AGAAGTCAGG | AACCATCACT | 780 |
| GAATTACTGG | CTGAAGATGG | AAAACCCGTC | AGCGTTGATA | CGCCTCTGTT | TACCATCGCT | 840 |

-continued

```
CCTTGAAATG AAGAAGCTGT CATTTTGAGC TGCTTCAGAA CATCATCAAA CTCCTGCTTA      900

TACCGACGTG CTGACAATCG TTAAAAGTAA TCATCTCGGT CAGGTTGGTT CGGGTTCGGC      960

TAATTATGTT TTTTTTTTCT TTTTCTCTCA ACTTTCTGAA CTCACTTTCT TTTGAGAATC     1020

GCGTAACATA TCAGTTATGC ATGTCTTTCG AACAAATCAG ACAAACTAAT AGTATGCTGT     1080

ACTATGAACT GCCCTATTAG GGTGAAAAAA AAAAAAAAAA AAAAAAAAAA AAA            1133

(2) INFORMATION FOR SEQ ID NO:6:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TCGACTGTGA GATTGTTATT CGAAAGAAGG AAGCTTTACA GCAGCAGCAA CCTGCACCAC       60

CAGCTCCGGT TTATCACTCT ATGCCTCCTC CTCCAACGGC AGGCTTTCCA ATGCCTCCAT      120

CTCAACCAGT TGCTCCTCCT GCTTCTACTC CCTCATCAGC GCCTGCAACA GAAAAACCAG     180

CAACCGCCCC TGCCTCTTCT GATCCTCCGC TCAAGAGTCC TATGGCTGGT ACTTTCTACA     240

GATCTCCTGG ACCCGGTGAA CCTCCTTTTG TCAAGGTTGG AGATAAGGTG CAGAAGGGTC     300

AAGTAGTTTG CATCATTGAA GCTATGAAAC TCATGAATGA GATTGAGGCT GAGAAATCAG     360

GAACCATCAC TGAACTACTG GCTGAAGATG GAAAACCGGT TAGCGTTGAC ACGCCTCTGT     420

TTACCATCGT GCCTTGAAGC GTCATTTTAG CTGGTTCAGA ACATCTTCAA AGTCTTGGTT     480

TATATCGACG GGCTGAAAAT CATTCAAGTA ATTGTTTCGG TTTTTTCTTT TTGCTTGAAC     540

TGTCACATTT TGTGTGAACC AGTTAACGTA TTAAAATTGC ATGTTTTTAG GATAATTTGG     600

ACAAATCAAT TCAGTTTACA GTGGGTTGTA CTATCTCCCC TGGTTTGATA TGATTTGTGT     660

TGTTCGGATG ATATAACTTT ATAGAAAGTG TTAGATTCAA AACGCAAAAA AAAAAAAAA      719
```

PLANT GENE ENCODING ACETYL COENZYME A CARBOXYLASE BIOTIN CARBOXYL CARRIER PROTEIN

This invention relates to a plant gene specifying the biotin carboxyl carrier protein (BCCP) a subunit of acetyl Coenzyme A carboxylase (ACCase) and to plant genomes genetically transformed with the said gene. Particularly, but not exclusively, the invention relates to ACCase BCCP genes from plants of the Brassica species, especially *Brassica napus* (oilseed rape) and control of expression of the gene in Brassica plants which are genetically transformed with the gene, a partial gene or its antisense configuration.

Two principal methods for the control of expression are known. These are referred to in the art as "antisense downregulation" and "sense downregulation" or "cosuppression". Both of these methods lead to an inhibition of expression of the target gene. Overexpression is achieved by insertion of one or more than one extra copies of the selected gene. Other lesser used methods involve modification of the genetic control elements, the promoter and control sequences, to achieve greater or lesser expression of an inserted gene.

In antisense downregulation, a DNA which is complementary to all or part of the target gene is inserted into the genome in reverse orientation and without its translation initiation signal. The simplest theory is that such an antisense gene, which is transcribable but not translatable, produces mRNA which is complementary in sequence to mRNA product transcribed from the endogenous gene: that antisense mRNA then binds with the naturally produced "sense" mRNA to form a duplex which inhibits translation of the natural mRNA to protein. It is not necessary that the inserted antisense gene be equal in length to the endogenous gene sequence: a fragment is sufficient. The size of the fragment does not appear to be particularly important. Fragments as small as 40 or so nucleotides have been reported to be effective. Generally somewhere in the region of 50 nucleotides is accepted as sufficient to obtain the inhibitory effect. However, it has to be said that fewer nucleotides may very well work: a greater number, up to the equivalent of full length, will certainly work. It is usual simply to use a fragment length for which there is a convenient restriction enzyme cleavage site somewhere downstream of fifty nucleotides. The fact that only a fragment of the gene is required means that not all of the gene need be sequenced. It also means that commonly a cDNA will suffice, obviating the need to isolate the full genomic sequence.

The antisense fragment does not have to be precisely the same as the endogenous complementary strand of the target gene. There simply has to be sufficient sequence similarity to achieve inhibition of the target gene. This is an important feature of antisense technology as it permits the use of a sequence which has been derived from one plant species to be effective in another and obviates the need to construct antisense vectors for each individual species of interest. Although sequences isolated from one species may be effective in another, it is not infrequent to find exceptions where the degree of sequence similarity between one species and the other is insufficient for the effect to be obtained. In such cases, it may be necessary to isolate the species-specific homologue.

Antisense downregulation technology is well-established in the art. It is the subject of several textbooks and many hundreds of journal publications. The principal patent reference is European Patent No. 240,208 in the name of Calgene Inc. There is no reason to doubt the operability of antisense technology. It is well-established, used routinely in laboratories around the world and products in which it is used are on the market.

Both overexpression and downregulation are achieved by "sense" technology. If a full length copy of the target gene is inserted into the genome then a range of phenotypes is obtained, some overexpressing the target gene, some underexpressing. A population of plants produces by this method may then be screened and individual phenotypes isolated. As with antisense, the inserted sequence is lacking in a translation initiation signal. Another similarity with antisense is that the inserted sequence need not be a full length copy. Indeed, it has been found that the distribution of over- and under-expressing phenotypes is skewed in favour of underexpression and this is advantageous when gene inhibition is the desired effect. For overexpression, it is preferable that the inserted copy gene retain its translation initiation codon. The principal patent reference on cosuppression is European Patent 465,572 in the name of DNA Plant Technology Inc. There is no reason to doubt the operability of sense/co-suppression technology. It is well-established, used routinely in laboratories around the world and products in which it is used are on the market.

Sense and antisense gene regulation is reviewed by Bird and Ray in Biotechnology and Genetic Engineering Reviews 9: 207–227 (1991). The use of these techniques to control selected genes in tomato has been descibed by Gray et.al., Plant Molecular Biology, 19: 69–87 (1992).

Gene control by any of the methods described requires insertion of the sense or antisense sequence, with appropriate promoters and termination sequences containing polyadenylation signals, into the genome of the target plant species by transformation, followed by regeneration of the transformants into whole plants. It is probably fair to say that transformation methods exist for most plant species or can be obtained by adaptation of avaliable methods.

For dicotyledonous plants the most widely used method is Agrobacterium-mediated transformation. This is the best known, most widely studied and, therefore, best understood of all transformation methods. The rhizobacterium *Agrobacterium tumefaciens,* or the related *Agrobacterium rhizogenes,* contain certain plasmids which, in nature, cause the formation of disease symptoms, crown gall or hairy root tumours, in plants which are infected by the bacterium. Part of the mechanism employed by Agrobacterium in pathogenesis is that a section of plasmid DNA which is bounded by right and left border regions is transferred stably into the genome of the infected plant. Therefore, if foreign DNA is inserted into the so-called "transfer" region (T-region) in substitution for the genes normally present therein, that foreign gene will be transferred into the plant genome. There are many hundreds of references in the journal literature, in textbooks and in patents and the methodology is well-established.

The effectiveness of Agrobacterium is restricted to the host range of the microorganism and is thus restricted more or less to dicotyledonous plant species. In general monocotyledonous species, which include the important cereal crops, are not amenable to transformation by the Agrobacterium method. Various methods for the direct insertion of DNA into the nucleus of monocot cells are known.

In the ballistic method, microparticles of dense material, usually gold or tungsten, are fired at high velocity at the target cells where they penetrate the cells, opening an aperture in the cell wall through which DNA may enter. The DNA may be coated on to the microparticles or may be added to the culture medium.

In microinjection, the DNA is inserted by injection into individual cells via an ultrafine hollow needle.

Another method, applicable to both monocots and dicots, involves creating a suspension of the target cells in a liquid, adding microscopic needle-like material, such as silicon carbide or silicon nitride "whiskers", and agitating so that the cells and whiskers collide and DNA present in the liquid enters the cell.

In summary, then, the requirements for both sense and antisense technology are known and the methods by which the required sequences may be introduced are known. What remains, then is to identify genes whose regulation will be expected to have a desired effect, isolate them or isolate a fragment of sufficiently effective length, construct a chimeric gene in which the effective fragment is inserted between promoter and termination signals, and insert the construct into cells of the target plant species by transformation. Whole plants may then be regenerated from the transformed cells.

An object of the invention is to provide a method and material for modulating expression of the ACCase BCCP subunit in plants.

According to the present invention there is provided a method of modifying the fatty acid production capacity of a plant comprising modulating the expression of the gene encoding the acetyl Coenzyme A carboxylase biotin carboxyl carrier protein.

Modulation may comprise overexpressing said gene by which may be achieved by stable insertion into the genome of the plant of one or more than one copy of an expressible gene construct coding for said protein.

On the other hand modulation may comprise downregulation of the expression of the said gene which may be achieved by stable insertion into the genome of the plant of an antisense gene construct containing a transcribable DNA sequence comprising a DNA complementary to all or part of the endogenous DNA sequence of the said gene. Alternatively, overexpression may be achieved by stable insertion into the genome of the plant of a sense gene construct containing a transcribable DNA comprising a fragment of the endogenous DNA sequence encoding the said gene.

The invention also provides a DNA having the nucleotide sequence selected from ID-1, ID-2, ID-3, ID-4, ID-5 or ID-6 and variants thereof permitting by the degeneracy of the genetic code.

Further, the invention provides a vector comprising a gene promoter operable in plants, a transcribable region comprising a DNA as claimed in claim 7 and a polyadenylation signal.

The present invention also provides a recombinant plant genome comprising one or more of the said DNAs.

Acetyl Coenzyme A carboxylase is a key enzyme in the pathway for the synthesis of fatty acids which are the components of the oil of oil producing crops such as oilseed rape. It is this enzyme which initiates the pathway, committing the precursor—acetyl CoA—to the fatty acid synthetic pathway by converting it to malonyl CoA by a carboxylation reaction.

Acetyl Coenzyme A carboxylase (ACCase) from *E. coli* is a dissociable multisubunit enzyme composed of biotin carboxylase and biotin carboxyl carrier protein (BCCP) subunits and carboxyl transferase α and β subunits. In mammals however the ACCase enzyme is composed of only one polypeptide containing all three functional domains.

In plants both forms of ACCase are present. A 220 kDa ACCase polypeptide containing all three functional domains has been purified from plant tissues and the corresponding genes cloned from sources such as rape, wheat and Arabidopsis. In addition a gene with significant sequence homology to the β subunit of *E. coli* transcarboxylase has been cloned from pea (Sasaki et al. 1993). This gene was isolated from chloroplast DNA. A dissociable multi-subunit ACCase is therefore present in plant plastids. Whereas the transcarboxylase β subunit gene is chloroplast encoded, the transcarboxylase α subunit, the biotin carboxylase subunit and the BCCP subunit are all nuclear encoded. Transcripts from the latter genes are therefore translated in the cytosol, and the polypeptides taken up into the plastids due to the presence of plastid targeted transit peptide sequences. Whereas techniques for down-regulation of the expression of the chloroplast encoded transcarboxylase gene are not yet available, it is possible to down-regulate expression of the nuclear encoded subunits by antisense or partial sense technologies described below.

This invention is principally concerned with genes encoding the biotin carboxyl carrier protein (BCCP) subunit of the dissociable plant ACCase. An object of the invention is to provide a gene specifying ACCase BCCP subunit in plants. Down-regulation of the expression of this gene, by antisense or partial sense technologies, will cause a down-regulation of total ACCase enzyme activity present in plant plastids.

The present invention also provides genetically transformed plants, plant cells and plant parts, containing a DNA of the invention or fragment thereof in sense orientation or a complete or partial sense or antisense variant thereof.

It is preferred that the plant be of a species which produces substantial quantities of oil, rather than starch. Such plant species are well known and are simply referred to as "oil-seed" crops and include amongst others, oilseed rape, canola, soya, sunflower, maize and palm (where oil is stored in both the seed and fruit tissues). Methods for the genetic transformation of many oil crops are known, for example, transformation by *Agrobacterium tumefaciens* methods are suitable for most. Such methods are well-described in the literature and well-known and extensively practised in the art.

In our International Patent Application Number WO 92/19747, published on 12th November 1992, we describe the biosynthesis of polyhydroxybutyrate from the substrate, acetyl-CoA. This activity involves three enzyme-catalysed steps. The three enzymes involved are β-ketothiolase, NADP linked acetoacetyl-CoA reductase, and polyhydroxybutyrate synthase, the genes for which have been cloned from *Alcaligenes eutrophus* (Schubert et al, 1988, J Bacteriol, 170). In our international application we describe the cloning of these three gene into oil-synthesising plants.

However, the synthesis of fatty acids which are the building blocks of plant oils utilise the substrate acetyl Coenzyme A which is the same substrate required by the polyhydroxyalkanoate genes. By virtue of the present invention we provide means for down-regulating fatty acid synthesis by reducing the expression of ACCase thereby leaving the acetyl CoA available for conversion to polyhydroxyalkanoates.

Methods for the regulation of gene expression are well-known in the art. Two principal methods are commonly employed, these being referred to loosely as 'sense' and "antisense" regulation. In antisense regulation a gene construct is assembled which, when inserted into a plant cell, results in expression of a messenger RNA which is of complementary sequence to the messenger produced by a target gene. The theory is that the complementary RNA sequences form a duplex thereby inhibiting translation to protein. The complementary sequence may be equivalent in length to the whole sequence of the target gene but a fragment is usually sufficient and is more convenient to handle. In sense regulation a copy of the target gene is inserted into the plant genome. Again this may be a full length or partial sequence. A range of phenotypes is obtained from which individuals in which the expression of the protein encoded by the target gene is inhibited may be identified and isolated as may individuals where expression of the gene product is increased. Sense regulation using partial sequences tends to favour inhibition. The mechanism is not well understood. Reference is made to European Patent Application No. 140,308 and U.S. Pat. No. 5,107,065 which are both concerned with antisense regulation and International Patent Application No. WO 90/12084 which describes sense regulation. The invention permits the following genetic modifications to be effected:

1. The clones of the invention may be used to probe plant DNA (genomic or cDNA libraries) to obtain homologous sequences. These may be truncated or full length cDNAs or genomic DNAs for ACCase BCCP subunit genes from, for example, wheat, or oil crops such as rape, canola, soya, sunflower, maize, oil palm and coconut.

2. cDNAs of rape seed ACCase BCCP subunit may be used in conjunction with a plant-recognised promoter to create an expression cassette (partial sense or antisense) for use in transforming rape plants to down-regulate production of the ACCase BCCP subunit. This will give plants with a lowered ACCase activity. Such plants will have a lower oil content or oil of altered quality. The same cassette can be used to down-regulate the production of ACCase BCCP subunit in other plants of the Brassica species. BCCP cDNAs isolated from other crops can be used to create expression cassettes (partial, sense or antisense) for use in transformation of these crops in order to modify the oil content.

Down-regulation of oil synthesis (in rape or other oil crops) can be used to divert the substrate, acetyl Coenzyme A, into synthesis of alternative storage materials such as starch, protein, or novel polymers introduced by genetic modification, for example polyhydroxyalkanoates.

3. Full length cDNAs or genomic DNAs of rape ACCase BCCP subunits, or full length cDNAs or genomic DNAs of ACCase BCCP genes from other oil crops, can be used in conjunction with their endogenous promoters, or with alternative plant recognised promoters to create novel expression cassettes. When transformed into rape plants, or plants of other oil crops, these cassettes could raise the total expression level of BCCP, or extend the period of expression of BCCP in the developing seed (or fruit). Such strategies could result in raising the level of oil stored by the said seed or fruit.

4. Genomic DNAs of rape ACCase BCCP subunit can be used to recover the promoter of the ACCase BCCP gene. This promoter can be used to generate RNA in a tissue-specific and developmentally regulated fashion. The promoter so generated may promote the expression of ACCase, or it may control the expression of a gene construct placed after it (for example the structural gene of a different enzyme) which will then be expressed specifically in the developing seed.

5. The full length cDNA and genomic DNA of rape ACCase BCCP subunit contains a sequence between the translation start site and the N-terminal sequence of the mature protein, known as a "transit peptide" sequence. This directs the gene product to the plastids and is cleaved off during import of the protein into the plastids. This transit peptide sequence may be used in gene fusions to direct different gene products to the plastids.

We have prepared a poly dT primed cDNA library derived from polyA+ tail mRNA from developing rape embryo. Scanning a GenBank data base revealed an Arabidopsis cDNA showing homology with the accB gene (BCCP subunit) from *E. coli*. The cDNA was obtained and a 600 bp insert was isolated. This was used to probe the rape embryo cDNA library. Partial length cDNA clones pBP1, pBP2, pBP3 and pBP7, specifying rape seed ACCase BCCP subunit, were thereby selected. Full length BCCP cDNA clones pBP4 and pBP6 were also identified. That the clones were indeed of the ACCase subunit was confirmed by the fact that the nucleotide sequences and the derived amino acid sequences showed substantial homology with the *E. coli* and Anabaena accB (BCCP subunit) genes.

The clones pBP1, pBP2, pBP3 and pBP7 have been deposited with the National Collection of Industrial and Marine Bacteria, 23 St Machar Drive, Aberdeen, AB2 1RY on Feb. 1, 1995: the accession numbers are NCIMB 40707, 40708, 40706 and 40705 respectively.

The invention will now be described with reference to the following sequences where:

SEQ-ID-NO-1 shows the DNA sequence of cDNA insert pBP1. The sequence contains a putative Biotin binding site from bases 478 to 493.

SEQ-ID-NO-2 is the DNA sequence of cDNA insert of pBP2. The sequence contains a putative Biotin binding site from bases 91 to 106.

SEQ-ID-NO-3 is the DNA sequence of cDNA insert of pBP3.

SEQ-ID-NO-4 is the DNA sequence of cDNA insert of pBP4.

SEQ-ID-NO-5 is the DNA sequence of cDNA insert of pBP6.

SEQ-ID-NO-6 is the DNA sequence of cDNA insert of pBP7.

Results

Northern Blot Analysis

In order to isolate the cDNA encoding the rape BCCP subunit, from the multi subunit form of ACCase we needed a hybridising probe. A data base was available which contained sequences from Arabidopsis EST cDNA's. After scanning the GenBank data base a sequence was identified that showed homology to the accB gene (BCCP subunit) from *E. coli*. Using the cDNA clone VCVDE 11 3' (GenBank ID Z25714) obtained from the Arabidopsis Biological Resource Center at Ohio State University we isolated the 600 bp insert. In order to check if the gene was actually present in rape and determine the full length transcript size the probe was used to hybridise to a Northern blot of Rape poly A+ tail mRNA. The dominant hybridising band was shown to be 1.3 kb in size. During embryogenesis the level of transcript was high initially, rising further to a peak at mid stage, followed by a large cut off in expression in the later stages. A much higher level of transcript was present in Embryo and root than in leaf (approx 20:1).

In order to study the mRNA expression of the BCCP genes which are thought to be involved in the de novo storage lipid synthesis, a developmental Northern blot was screened. Each lane on the blot had an equal amount of root, leaf or embryo poly(A)+ mRNA from different stages of *B. napus* embryogenesis. The results indicated that during embryogenesis, BCCP mRNA expression rose steeply, peaking during the middle portion of embryogenesis. Although there was a notable amount of BCCP mRNA present in the root, there was a comparatively low level in the leaf.

cDNA Cloning

The Northern blot data suggested that a rape embryo cDNA library derived from Rape poly A+ tail mRNA was the most suitable to screen for a BCCP clone. Approximately 150,000 recombinant plaques were screened. The hybridising plaques were taken through three rounds of screening at which point they were plaque pure.

Anti biotin Analysis

Since approximately twenty clones were taken through three rounds of screening an early indication of the clone identity was needed. The library that was used for screening was constructed using the expression vector λZAP II. It has been shown previously that λZAP II clones induced to express the encoded protein can be biotinylated by the E. coli host provided that the biotinylation site is present in the expressed protein. Providing at least one of the inserts is in frame and in the right orientation then the clone could be identified by this biotinylation method for preferential sequencing. Positive clones from the library screens were induced to express their protein by IPTG treatment and screened using peroxidase linked streptavidin/ECL detection system.

Protein Blot Data

The transcript size from Northern analysis showed that the full length mRNA encoding the BCCP protein was 1.3 kb. This would encode a polypeptide of approximately 25 kDa. In addition, it was shown that expression in embryo was approximately 20× that of leaf. Using fresh whole protein extracts from rape seed and leaf a Western blot was carried out using Iodine 125 ($I^{125}$) labelled Sreptavidin to identify biotin containing proteins. A biotin containing protein of approximately 35 kDa was seen that was present in rape embryo but not leaf extracts. Since this data conforms with that of the Northern analysis data the protein may represent the product of the rape BCCP gene.

Sequence Analysis

Positive clones from the library screens were sequenced. Six clones were identified and denoted pBP1, pBP2, pBP3 pBP4, pBP6 and pBP7.

The sequence of pBP1 is shown as SEQ-ID-NO-1. The sequence contains a putative biotin binding site from bases 478 to 493. pBP1 shows considerable amino acid sequence homology with the BCCP gene of Anabaena and E. coli. The sequence of pBP2 is shown as SEQ-ID-NO-2. The putative biotin binding site is from bases 91 to 106. pBP2 shows considerable amino acid homology with pBP1. The sequence of pBP3 is shown as SEQ-ID-NO-3. The sequences pBP4 and 6 are shown as SEQ-ID-NO-4 and SEQ-ID-NO-5 respectively. The sequence of pBP7 is shown as SEQ-ID-NO-6. pBP7 shows considerable amino acid sequence homology with the BCCP gene of E.coli.

Materials and Methods cDNA Library Construction i) cDNA library used was generated using Poly (A) +mRNA isolated according to the method of Logemann et al from mid stage developing Jet neuf rape embryos (harvested at approximately 35 days post anthesis). The first strand synthesis was carried out using poly dT oligo primers according to the manufacturers' instructions (Amersham International). The resulting cDNA's generated were directionally cloned into the EcoRI/Xhol sites of λ-ZAP II as recommended by the manufacturers (Stratagene). The host bacteria used was XL-1 Blue (Stratagene).

Probe Preparation and Labelling cDNA probes for screening the rape libraries were generated by the appropriate restriction endonuclease digestions of plasmid DNA. The DNA fragment required was separated from vector DNA by TAE agarose electrophoresis and isolated using the GeneClean II kit (Bio 101) or by freezing and ultrafiltration.

The probes (200–300 ng) were radio-labelled with [$\alpha^{32}$P] dCTP using the Megaprime kit as recommended by the manufacturers (Amersham International) to a level of 5×10⁹ cmp/μg. Un-incorporated label was removed using Biospin chromatography columns (Biorad).

Library Screening 150,000 plaque forming units were screened as previously described. The filters were hybridised at 65° C. Plasmid rescue of cDNA clones was carried out as described in the Stratagene protocol for "in vivo excision of pSK from λ-ZAP II".

Sequencing of DNA Clones

Sequencing was carried out using an Applied Biosystems Inc. 373A DNA sequencer (Durham University sequencing service, Ms J Bartley). Both forward and reverse primers (−21m13 and M13RPI) were used initially for all clones. Nested deletions were generated as recommended by Pharmacia (d.s. Nested Deletion Kit) and sequenced using a combination of forward and reverse primers and synthesised oligonucleotide primers. Primers were made using a 381A DNA synthesiser (Applied Biosystems Inc). Computer analysis of DNA sequence will be carried out using the SEQNET package from the SERC facility at Daresbury and DNA Strider.

Northern Blot Analysis

Poly A+ mRNA was prepared from either 5 g young leaf or 5 g embryo's harvested at 15, 22, 29, 36, 42 and 49 days post anthesis using the recommended procedure (Pharmacia mRNA purification kit). 1–5 μg was loaded onto a 1% formamide/formaldehyde agarose gel for electrophoresis. The Northern blot procedure was carried out as described previously.

Expression of λ clones and Biotinylation Detection

Approximately 2×105 p.f.u. were plated onto each of 3 large NZYM plates using E. coli KW251 as the host strain, after growth at 42° C. until "pin-prick" size plaques appear (approximately 34 hrs), the plates were overlayed with nitrocellulose filters (20×20 cm) presoaked in 10 mMIPTG and allowed to dry. Growth of the plaques was then continued overnight at 37° C.

After overnight incubation the filters were removed and washed briefly in TBS (50 mM Tris pH 7.5, 0.2 M Na Cl, 0.5 mM CaCl2, 50 mM MgCl2). The membranes were blocked for 2 hours in TBS/1% (w/v) haemoglobin at 30° C. followed by a further 2 hours in block buffer/Peroxidase linked streptavidin (Sirotech). The membranes were then rinsed extensively in TBS/0.05% Tween 20 at room temperature.

The ECL visualisation system was used to identify positive clones, as described by the manufacturers (Amersham).

Preparation of Crude Extracts

Fresh plant material was frozen in liquid nitrogen and ground frozen by mortar and pestle. The resulting fine powder was placed in eppendorf and 4 volumes of XI sample loading buffer added. The slurry was immediately boiled for 5 minutes and centrifuged for 10 minutes in a bench top microfuge centrifuge. The supernatant was removed and stored at −80° C. in aliquots. Protein samples were used up to 2 months after preparation.

Western Blotting

After SDS PAGE, proteins were blotted onto ProBlot (ABI) by semi-dry blotting. Marker proteins were located by Ponceau staining in accordance with the manufacturers instructions. Membranes were blocked with 1% Haemoglobin, 20 mM Tris pH 7.2 170 mM NaCl for 1 hour with constant mixing. 125 linked streptavidin was added at a 1:200 ratio and incubated at room temperature overnight. The blot was extensively washed with 0.2% Nonidet P40, blocking solution with several changes of wash solution over 1 hour. The blot was exposed to X-ray film for 1–7 days.

The western blots provided results indicating the BCCP levels. In the absence of specific BCCP antibodies, and because BCCP is biotinylated in vivo, biotin-specific antiserum was used to generate biotin specific antibodies. Keyhole limpet haemcyanin was coated with biotin and used as an antigen in rabbits. To minimise false background signals on the Western blot, all the antibodies generated were affinity-purified. This was achieved by column chromatography on a biotin-agarose matrix. The theoretical sizes of the BCCP protein bands were predicted at 22.7 kDa and 21.9 kDa from the two longest clones being SEQ-ID-NO-4 and SEQ-ID-NO-5. Previous work however, describing the prokaryotic BCCP studies, showed that the proline/alanine-rich region of E. coli BCCP confers an SDS gel anomaly. The protein runs at 35% less mobility than that predicted from the sequence. Since the B. napus BCCP sequence also contains a similar proline/alanine-rich region, the exact molecular mass could not be predicted from SDS gel mobility. Experiments using the antibodies have shown that the one biotinylated protein in pea chloroplasts was the 35 kDa BCCP sub unit of ACCase. Similarly, Western blots of B. napus chloroplast proteins showed that only one biotinylated protein resides within the chloroplast. It is therefore highly probable that the 35 kDa bands shown on the Western blots of the B. napus root, leaf and embryo extracts, are BCCP. Purification of plastids from rapeseed embryos also revealed that the biotinylated polypeptide is localised within the plastid. Furthermore, although the same levels of protein were initially loaded onto the gels, the BCCP levels were low in both root and leaf in comparison with that in the embryo.

What is claimed is:

1. An isolated DNA having the nucleotide sequence selected from SEQ ID NO: 1, SEQ ID NO: 2, SEQ ID NO: 3, SEQ ID NO: 4, SEQ ID NO: 5; and SEQ ID NO: 6 and variants thereof permitted by the degeneracy of the genetic code; and complementary sequences thereof.

2. A vector comprising a gene promoter operable in plants, a transcribable region comprising a DNA as claimed in claim 1 and a polyadenylation signal.

3. A plant genome transformed with a vector as claimed in claim 2.

4. A method of modifying the fatty acid production capacity of a plant comprising modulating the expression of the gene encoding the acetyl Coenzyme A carboxylase biotin carboxyl carrier protein in a plant the genome of which has been stably transformed with a vector as claimed in claim 1.

5. A method as claimed in claim 4, in which modulation comprises overexpressing said gene.

6. A method as claimed in claim 5 in which overexpression of the said gene is achieved by stable insertion into the genome of the plant of one or more than one copy of an expressible gene construct coding for said protein.

7. A method as claimed in claim 4, in which modulation comprises downregulation of the expression of the said gene.

8. A method as claimed in claim 7, in which downregulation of the said gene is achieved by stable insertion into the genome of the plant of an antisense gene construct containing a transcribable DNA sequence comprising a DNA complementary to all or part of the endogenous DNA sequence of the said gene.

9. A method as claimed in claim 7, in which downregulation of the said gene is achieved by stable insertion into the genome of the plant of a sense gene construct containing a transcribable DNA comprising a fragment of the endogenous DNA sequence encoding the said gene.

* * * * *